United States Patent [19]

Himmelstein et al.

[11] Patent Number: 4,489,056

[45] Date of Patent: Dec. 18, 1984

[54] ACID ANHYDRIDES AS RATE CONTROLLING AGENT FOR THE EROSION OF POLYMERS WHICH LATTER POLYMERS HAVE BENEFICIAL SUBSTANCES DISPERSED THROUGHOUT THEIR MATRIX OR WHERE THE POLYMER MATRIX SURROUNDS THE BENEFICIAL SUBSTANCE

[75] Inventors: Kenneth J. Himmelstein; Takeru Higuchi, both of Lawrence, Kans.

[73] Assignee: Merck & Co., Inc., Rahway, N.J.

[21] Appl. No.: 393,990

[22] Filed: Jun. 30, 1982

[51] Int. Cl.³ .......................... A61K 9/22; A61K 9/26; A61K 9/52; A61K 31/74
[52] U.S. Cl. ........................................ 424/22; 424/19; 424/78
[58] Field of Search .............................. 424/19, 22, 78

[56] References Cited

U.S. PATENT DOCUMENTS 4,093,709  6/1978  Choi et al. ............................ 424/19
4,304,767  12/1981  Heller et al. .......................... 424/78

Primary Examiner—Stanley J. Friedman
Attorney, Agent, or Firm—R. Brent Olson; Michael C. Sudol, Jr.

[57]   ABSTRACT

The invention relates to the use of an acid anhydride incorporated as a latentiated catalyst in poly(ortho ester) and other polymers such that upon exposure to aqueous environments the acid anhydride generates the corresponding acid which catalyzes the matrix erosion. The releasing rate of a loaded drug substance incorporated into or surrounded by the poly(ortho ester) or other polymers can be controlled in that the drug is released as the poly(ortho ester)s or other polymer is eroded by action of the acid anhydride incorporated therein.

9 Claims, No Drawings

ACID ANHYDRIDES AS RATE CONTROLLING AGENT FOR THE EROSION OF POLYMERS WHICH LATTER POLYMERS HAVE BENEFICIAL SUBSTANCES DISPERSED THROUGHOUT THEIR MATRIX OR WHERE THE POLYMER MATRIX SURROUNDS THE BENEFICIAL SUBSTANCE

BACKGROUND OF THE INVENTION

There has been a long need in the field of drug delivery devices to have a drug released in the human body at the place where it is most therapeutically effective and to have said drug released in the body in a controlled manner over a long period of time.

There is art showing that poly(ortho ester)s and other polymers can be used as a matrix for drug release; however, there is no description in any of this art of the use of acid anhydrides as catalysts to promote the polymer erosion in a controlled fashion.

Also, the release of norethindrone from poly(ortho ester)s slabs has been described in the prior art. However, in this system a water-soluble salt such as sodium chloride and the like was incorporated into the polymer and the proposed mechanism for drug release in this case was osmotic imbibing of water, causing the matrix to swell and burst. The drug release was not controlled by polymer erosion but by a swelling process.

SUMMARY AND DESCRIPTION OF THE INVENTION

This invention relates to the use of acid anhydrides as rate-controlling agents for the erosion of poly(ortho ester)s and other polymers to which therapeutically effective drug substance(s) or other beneficial substances (hereafter collectively referred to as biologically active agents) have been added are surrounded by such polymers and anhydride mixtures so that as said polymer is eroded, the drug or other substance is released in a controlled manner.

It has been noted that poly (ortho ester)s and some other polymer linkages herein described are sensitive toward acids but relatively stable at neutral or basic pH. Thus, an acid anhydride which is incorporated as a latentiated catalyst in the polymer matrix would generate a corresponding acid upon exposure to aqueous environments and subsequently catalyze the matrix erosion. If, in addition, a pharmaceutical or therapeutic agent or drug is incorporated in the matrix of the polymer, it can be seen that the drug can be relesed at a predictable rate from the polymer matrix as the polymer matrix is eroded by action of the acid generated from the incorporated acid anhydride. Also the polymer/acid anhydride matrix could surround the drug or beneficial substance whereby the drug or substance will be released when the polymer/acid hydride matrix coating is erroded. The proposed mechanism for breakdown and erosion of the polymer [here a poly(ortho ester) is shown] can be shown by the following equations where R' is as defined further along.

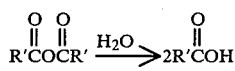

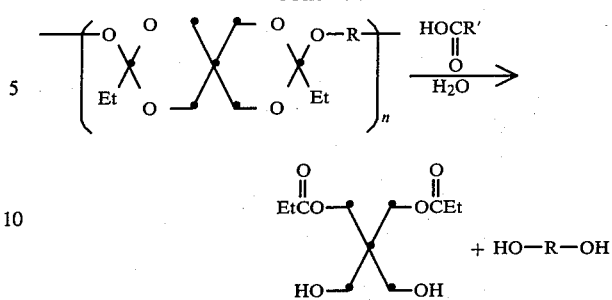

The rate of polymer matrix erosion and subsequently the rate of release of any drug substance or pharmaceutically therapeutic substance incorporated into or surrounded by the matrix can be controlled by choosing the proper acid anhydride or combination of acid anhydrides. This can be done and the rate of erosion can be correlated with the pKa of the corresponding acid. Also, the concentration of the acid anhydride(s) incorporated into the polymer matrix will control the rate of erosion of the polymer matrix and subsequently the rate of release of the drug substance incorported therein. We have observed a linear relationship between the concentration of the acid anhydride incorporated and the rate of release of the drug substance and rate of erosion of the polymer when the drug or beneficial substance is incorporated in the polymer/acid anhydride matrix.

When the drug or beneficial substance is surrounded or coated by the polymer/acid anhydride matrix, the drug or beneficial substance can be discharged when the matrix erodes in a predictable time frame.

In a more detailed description of the invention, the following types of polymers can be used and also the following types of acid anhydrides can be used. Also there is described the type of pharmaceuticals, therapeutic agents or drugs or beneficial substances which can be incorporated into or surrounded by the matrix of said polymer to be released by reaction of the acid anhydride to form the corresponding acid which upon exposure to aqueous environments subsequently catalyzes the matrix erosion.

The polymers which can be used in our invention are all those described in U.S. Pat. No. 4,304,767 to Heller and U.S. Pat. No. 4,093,709 to Choi and Heller and others described below.

Examples of the polymers covered in these two patents and which are applicable to our invention are:

1. Polymers of di(or higher functionality) keteneacetals and polyols which have a repeating mer unit of

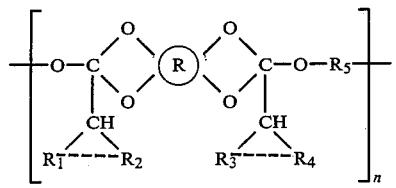

wherein n is an integer substantially greater than 10; wherein $R_1$ and $R_2$ are hydrogen or the same or different essentially hydrocarbon groups and may be separate groups or may form parts of a cyclic group; R is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains, and wherein R may be a single quadrivalent radical attached to all the interim acetal forming oxygen atoms, may be a spiro structure, may be an open chain aliphatic group, or may contain a carbocyclic group. Additionally, $R_5$ may contain some mer units that are alkylene or contain a carbocyclic group. Also included are polymers having the repeat units

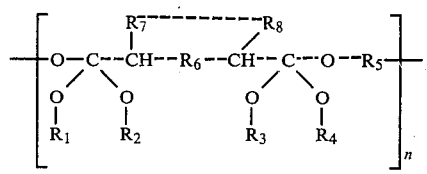

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_a$ wherein a is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains are also part of our invention. The group

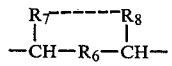

may be selected from the classic alkylene end groups containing a carbocyclic ring.

2. Poly(orthoester) or polyorthocarbonate polymers of the formula:

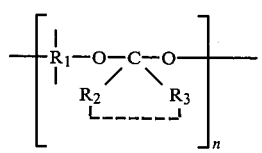

wherein $R_1$ is a multivalent hydrocarbon radical, $R_2$ and $R_3$ are hydrocarbon radicals with at least one of $R_2$ and $R_3$ are hydrocabron radicals with at least one of $R_2$ or $R_3$ bonded to the dioxycarbon through an oxygen linkage and n is a repeated mer unit.

3. Other broad classes of polymers to which this invention is applicable are those polymers with backbone functionalities which are sensitive to acid. Examples of these include polyacetals and polyketals of the formula:

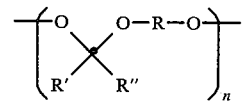

wherein
R′, R″=H, alkyl or aryl
R=alkylene, arylene and
n is a repeating mer unit.

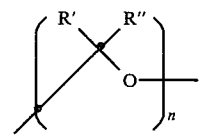

wherein
R′, R″=H, alkyl or aryl and
n= is a repeating mer unit.
and

4. Polyesters such as polylactate, polyglycolate, polycaprolactones and random co-polymers of the formulae:

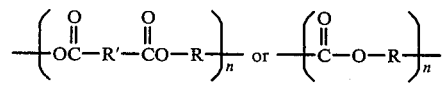

wherein n is a repeating mer unit and R and $R^1$ are as defined in 3 above.

The type of acid anhydrides which can be used in the invention are shown below.

I. 1. Monobasic carboxylic:

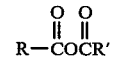

R, R′ are hydrogen or saturated or unsaturated hydrocarbon radicals containing up to 50 carbon atoms including aliphatic and aromatic groupings.

2. Dibasic carboxylic anhydrides of the type
i. cyclic

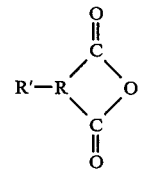

wherein $R=(CH_2)_n$ where (n=2-4) and R′ is as defined in 1 above for the anhydrides.

ii. polymeric

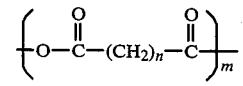

wherein n is 4 to 50 and m is a repeating mer unit.

3. sulfonic and sulfenic anhydrides of the formula $$RSO_n-O-SO_nR \qquad a.$$

-continued or b. 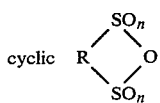
cyclic wherein
R is as defined above in No. 1 for anhydrides and n is 1 or 2.

4. mixed function anhydrides of the general formula

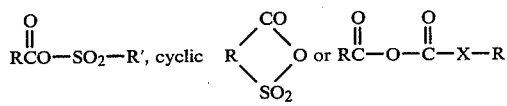

wherein
R and R' are as defined in No. 1 for anhydrides above and
X is O or S.

5. Inorganic acid anhydrides such as polyphosphoric anhydride.

Specific examples of acid anhydrides which are described above and which can be incorporated into the polymer matrix are:

1. Aliphatic, monobasic: Acetic, propionic or butyric anhydride.
2. Cyclic dibasic:
   saturated: succinic, glutaric, methylsuccinic or adipic anhydrides
   unsaturated: maleic or citraconic anhydrides
3. Aromatic: Benzoic anhydride
4. Aromatic dibasic: phthalic anhydride or polyterphthalic anhydride
5. Polymeric: polyadipic or polysebasic anhydride
6. Sulfonic: phenyl sulfonic or

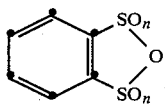

wherein n=1–2 or

7. Mixed function anhydrides such as o-sulfobenzoic or 3-sulfopropionic anhydride.

Suitable drugs (therapeutics) and beneficial substances (biologically active agents) for incorporation into or to be surrounded by the polymer matrix to be used with this invention and to be released to an aqueous environment include without limitation, the following:

1. Protein drugs such as insulin;
2. Desensitizing agents such as ragweed pollen antigens, hay fever pollen antigens, dust antigen and milk antigen;
3. Vaccines such as smallpox, yellow fever, distemper, hog cholera, fowl pox, antivenom, scarlet fever, dyptheria toxoid, tetanus toxoid, pigeon pox, whooping cough, influenzae, rabies, mumps, measles, poliomyelitis, Newcastle disease, etc.;
4. Anti-infectives, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole, cefoxitin; anti-virals including idoxuridine; and other anti-infectives including nitrofurazone and sodium propionate;
5. Antiallergenics such as antazoline, methapyrilene, chlorpheniramine, pyrilamine and prophenpyridamine;
6. Steroidal anti-inflammatory agents such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;
7. Decongestants such as phenylephrine, naphazoline, and tetrahydrazoline;
8. Miotics such as pilocarpine, eserine salicylate, carbachol, diisopropyl fluorophosphate, phospholine iodide, and demecarium bromide;
9. Anticholinergics such as atropine sulfate, cyclopentolate, homatropine, scopolamine, tropicamide, eucatropine, and hydroxyamphetamine;
10. Sympathomimetics such as epinephrine;
11. Sedatives and Hypnotics such as pentabarbital sodium, phenobarbital, secobarbital sodium, codeine, (α-bromoisovaleryl)urea, carbromal;
12. Psychic Energizers such as 3-(2-aminopropyl)indole acetate, 3-(2-aminobutyl)indole acetate and amitriptyline;
13. Tranquilizers such as reserpine, chlorpromazine, thiopropazate and perphenazine;
14. Androgenic steroids such as methyltestosterone and fluorymesterone;
15. Estrogens such as estrone, 17 β-estradiol, ethinyl estradiol, and diethyl stilbesterol;
16. Progestational agents such as progesterone, megestrol, melengestrol, chlormadinone, ethisterone, norethynodrel, 19-nor-progesterone, norethindrone, medroxyprogesterone and 17 β-hydroxy-progesterone;
17. Humoral agents such as the prostaglandins, for example $PGE_1$, $PGE_2$ and $PGF_2$;
18. Antipyretics analgesics such as aspirin, sodium salicylate, salicylamide, and diflunisal;
19. Antispasmodics such as atropine, methantheline, papaverine, and methscopolamine bromide;
20. Antimalarials such as the 4-aminoquinolines, 8-aminoquinolines, chloroquine, and pyrimethamine;
21. Antihistamines such as diphenhydramine, dimenhydrinate, tripelennamine, perphenazine, and chlorophenazine;
22. Cardioactive agents such as dibenzhydroflumethiazide, flumethiazide, hydrochlorothiazide chlorothiazide, and aminotrate;
23. Non-steroidal anti-inflammatory agents such as indomethacin and sulindac;
24. Antiparkinsonian agents such as L-dopa;
25. Antihypertensive agents such as methyldopa;
26. β-Adrenergic blocking agents such as propanolol and timolol;
27. Nutritional agents such as vitamins, essential amino acids and essential fats.

Other drugs having the same or different physiological activity as those recited above can be employed in drug-delivery systems within the scope of the present invention.

Other benificent compounds which can be released in a controlled manner over time can also be incorporated in the present invention. These include but are not limited to herbicides, pesticides, fertilizers, antifouling agents, biocides (germacides). One skilled in the art would realize that any beneficial substances which are released to the aqueous atmosphere can be used in this invention.

Drugs or therapeutically beneficial substances can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug or beneficial substance incorporated into the polymer matrix will vary greatly depending on the particular drug, the desired therapeutic effect and the time span in which the polymer matrix is eroded to release the particular drug. Thus, there is no critical upper limit on the amount of drug incorporated in the polymer matrix and the lower limit will also depend on the activity of the drug and the time span for the erosion of the polymer and subsequently the drug release. Thus, it is not practical to define a range for the therapeutically effective amount of drug to be incorporated in the novel polymer matrixes and acid anhydride combinations of the instant invention.

Generally, the amount of acid anhydride or anhydrides incorporated into the polymer will be dependent upon the release duration of the drug or beneficial substance, and the particular acid anhydride used but would generally be in the range of slightly more than 0% to a maximum of about 25% of the polymer by weight.

Also in the case of the drug or other beneficial substance incorporated into the polymer/acid anhydride matrix as stated above, the amount of drug or beneficial substance will depend on the type of drug or substance for the condition being treated and can generally be up to 70% of the polymer/acid anhydride matrix by weight.

The drug or beneficial substance can be administered in various ways and shapes. For example, the polymer-/acid anhydride/drug or beneficial substance can be incorporated into disc-shaped devices, rods or sheets for under the skin implantation, spherical shapes and the like. Those skilled in the art would realize that the invention can be incorporated in any shaped device for the particular application it is being used for.

The above described devices can be prepared by, for example:

1. Methods of preparation include: (1) Dissolution of components in solvent, evaporation of solvent, compression of matrix; (2) Mechanical milling of polymer, anhydride and drug or beneficial substance followed by compression; (3) Melt mixing of polymer, anhydride and drug or beneficial substance. In all cases, after mixing, standard pharmaceutical technology is used to make the dosage form.

In order to control the rate of release of the drug or beneficial substance in a programable manner, one can laminate layers wherein the polymer, acid anhydride and drug or beneficial substance in each laminate layer are varied in concentration or contain different species of each component.

Multiple anhydrides can be incorporated into the polymer to allow time variable or geometric considerations to be achieved. Additionally, the concentration of acid anhydride can be varied as a function of position in the matrix.

At least enough water must be present in contact with the device to react with the acid anhydride and the polymer to cause degradation. Water in excess of this amount will not materially effect the performance of the invention.

In order to better describe this invention, there is follows an example showing the concepts of the invention.

EXAMPLE 1

980 mg Poly(ortho ester) were dissolved in 20 ml methylene chloride. To the solution, acetone or methylene chloride solutions containing 20 mg of timolol maleate and 2, 3, 4 and 5 mg, respectively of maleic anhydride were added. The solvents were evaporated under reduced pressure. The residue was cut into small pieces and compressed into discs by a Carver Press ® at 5000 lbs pressure, at 60° C. temperature and for 5 minutes. The disc was mounted on a matched rotor, immersed in pH 7.4 buffer at 37° C. and rotated at 120 rpm. The appearance of timolol maleate was followed spectrophotometrically. The drug release curve was sigmoidal with a lag phase followed by nearly zero-order release and then a depleting phase. The release rate can be controlled by amounts and types of anhydride or anhydrides incorporated. Typical data for this example are shown as follows:

| Amount of Maleic Anhydride incorporated in polymer matrix* (%) by weight | Rate of release of timolol maleate** (mg/hr) |
| --- | --- |
| 0.2 | .115 |
| 0.3 | .196 |
| 0.4 | .228 |
| 0.5 | .287 |

*HD-DETOSU/t-CDM-DETOSU (7:3 blend); 70:30 physical blend of the following copolymers: 3,9-Bis(ethylidene)2,4,8,10-tetraoxospiro [5,5]undecane (DETOSU) and hexane diol and DETOSU-trans-cyclohexanedimethanol.
**At 2% (w/w) Timolol Maleate Following dissolution rate testing for each composition, any blend of polymer, acid anhydride and drug or beneficial agent can be made to achieve the desired release characteristics for the drug or beneficial agent.

The above description and example should be considered an illustration of this invention and not a limitation thereof.

What is claimed is:

1. A controlled release device for the delivery of drugs or other biological beneficial substances which comprises:
   (a) A poly(orthoester);
   (b) an erosion catalyzing amount up to a maximum of about 25 percent, by weight, based on (a), or at least one acid anhydride selected from the group consisting of a monobasic carboxylic anhydride, a cyclic dibasic carboxylic anhydride, and a polymeric carboxylic anhydride, incorporated within the matrix of said poly(orthoester); and
   (c) an effective amount up to 70 percent, by weight, based on (a) and (b), of a drug or other biological beneficial substance incorporated within or to be surrounded by the matix of said poly(orthoester), such that when said release device is exposed to aqueous environments, the matrix of said poly(orthoester) slowly erodes and said drug or beneficial substance is released in a controlled manner.

2. A controlled release device for the delivery of drug or other biological beneficial substances which comprises:
 (a) a poly(orthoester);
 (b) an erosion catalyzing amount up to a maximum of about 25 percent, by weight, based on (a), dibasic anhydride; and
 (c) up to 70 percent, by weight, based on (a) and (b), of a β-adrenergic blocking agent.

3. A controlled drug release device of claim 1, wherein said poly(orthoester) is a polymer of Di (or a higher functionality) ketene acetals and polyols of the formula

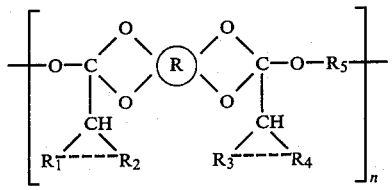

wherein n is an integer substantially greater than 10; and wherein $R_1$ and $R_2$ are hydrogen or the same or different essentially hydrocarbon groups and may be separate groups or may form parts of a cyclic group; R is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains, and wherein R may be a single quadrivalent radical attached to all the interim acetal forming oxygen atoms, may be a spiro structure, may be an open chain aliphatic group, or may contain a carbocyclic group and wherein additionally, $R_5$ may contain some mer units that are alkylene or contain a carbocyclic group and including polymers having the repeat units

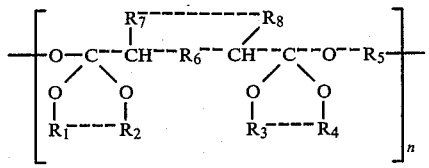

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_a$ wherein a is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains and wherein the group

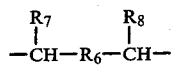

may be selected from the classic alkylene end groups containing a carbocyclic ring.

4. A controlled relese device of claim 1 wherein said poly(orthoester) is a polyorthocarbonate of the formula

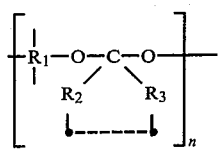

wherein $R_1$ is a multivalent hydrocarbon radical, $R_2$ and $R_3$ are hydrocarbon radicals with at least one of $R_2$ and $R_3$ are hydrocarbon radicals with at least one of $R_2$ or $R_3$ bonded to the dioxycarbon through an oxygen linkage and n is a repeating mer unit.

5. A controlled release device of claim 1 wherein the anhydride is a monobasic carboxylic anhydride of the formula:

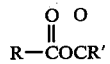

wherein R, R' are hydrogen or saturated or unsaturated hydrocarbon radicals containing up to 50 carbon atoms.

6. A controlled release device of claim 1 wherein the anhydride is a dibasic carboxylic anhydride of the formula:

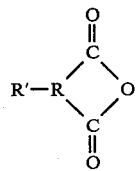

wherein $R=(CH_2)_n$ where (n=2-4): and R' is hydrogen or a saturated hydrocarbon radical containing up to 50 carbon atoms.

7. A controlled release device of claim 1 wherein the anhydride is a polymer anhydride having a repeating unit of the formula:

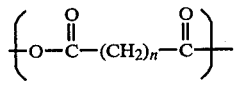

wherein n is 4–50.

8. A controlled drug release device of claim 1 wherein the drug or biological beneficial substance is a protein drug, a desensitizing agent, a vaccine, an anti-infective, an antiallergenic, a steroidal anti-inflammatory, a decongestant, a miotic, an anticholinergic, a sympathomimetic, a sedative; a hypnotic, a psychic energizer, a tranquilizer, an androgenic steroid, an estrogen, a progestational agent, a humoral agent an antipyretic analgesic, an antispasmotic, an antimalarial, an antihistamine, a cardioactive agent, a non-steroidal anti-inflammatory, an antiparkinsonian agent, an antihypertensive agent, a β-adrenergic blocking agent, a nutritional agent, a herbicide, a pesticide, a biocide, a fertilizer or an antifouling compound.

9. A controlled release device of claim 1 composed of laminates of polymer matrices and anhydride(s).

* * * * *